United States Patent [19]
Khairkhahan et al.

[11] Patent Number: 5,409,458
[45] Date of Patent: Apr. 25, 1995

[54] GROOVED BALLOON FOR DILATATION CATHETER

[75] Inventors: Alexander K. Khairkhahan, San Diego; Darryl A. Anderson, Riverside; Robert Ndondo-Lay, San Diego, all of Calif.

[73] Assignee: Medtronic, Inc., Minneapolis, Minn.

[21] Appl. No.: 149,887

[22] Filed: Nov. 10, 1993

[51] Int. Cl.⁶ ............................................. A61M 29/00
[52] U.S. Cl. ....................................... 604/96; 606/194
[58] Field of Search ................... 606/192, 194; 604/96, 604/101

[56] References Cited

U.S. PATENT DOCUMENTS

| | | | |
|---|---|---|---|
| 4,762,129 | 8/1988 | Bonzel | 128/344 |
| B1 4,762,129 | 7/1991 | Bonzel | 606/194 |
| 4,983,167 | 1/1991 | Sahota | 606/194 |
| 5,040,548 | 8/1991 | Yock | 128/898 |
| 5,061,273 | 10/1991 | Yock | 606/194 |
| 5,087,246 | 2/1992 | Smith | 604/96 |
| 5,090,957 | 2/1992 | Moutafis et al. | 604/96 |
| 5,116,305 | 5/1992 | Mider et al. | 600/18 |
| 5,141,494 | 8/1992 | Danforth et al. | 604/96 |
| 5,147,302 | 9/1992 | Euteneuer et al. | 604/103 |
| 5,180,367 | 1/1993 | Kontos et al. | 604/101 |
| 5,226,887 | 7/1993 | Farr et al. | 604/96 |
| 5,232,446 | 8/1993 | Arney | 604/96 |
| 5,320,605 | 6/1994 | Sahota | 604/101 |

Primary Examiner—Corrine Maglione
Attorney, Agent, or Firm—Dianne M. F. Plunkett; Harold R. Patton

[57] ABSTRACT

A dilatation catheter having a balloon (20) of unique and novel configuration which enhances critical properties of the catheter. In at least one section (26), the balloon (20) has a substantially semi-circular cross section when in an uninflated, unwrapped condition. A groove (28) is formed in the resulting flat surface (30) of the balloon (20) accommodate an elongate guide wire lumen (40) and improves fold memory. The guide wire lumen (40) extends along and beside a distal section (23) of the catheter, and is bonded near its distal end into the groove (28) in the balloon (20). At the distal end of the groove (28), the balloon (20) is configured such that the guide wire lumen (40) passes through the balloon wall, such that the distal end of the lumen is disposed in the interior inflation chamber of the balloon (20). In this way, the guide wire (42) follows an essentially straight path in the region of the balloon (20).

3 Claims, 5 Drawing Sheets

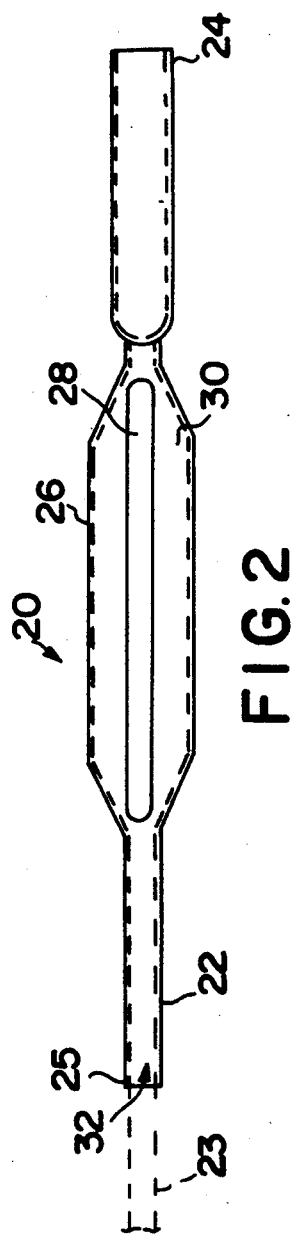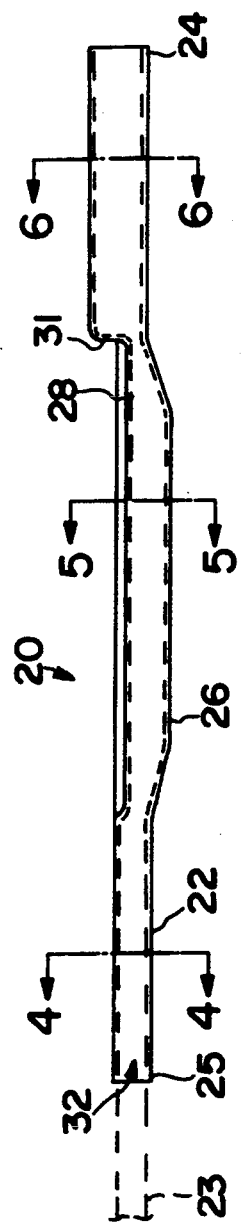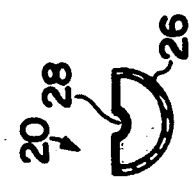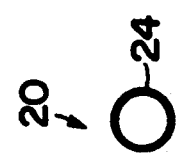

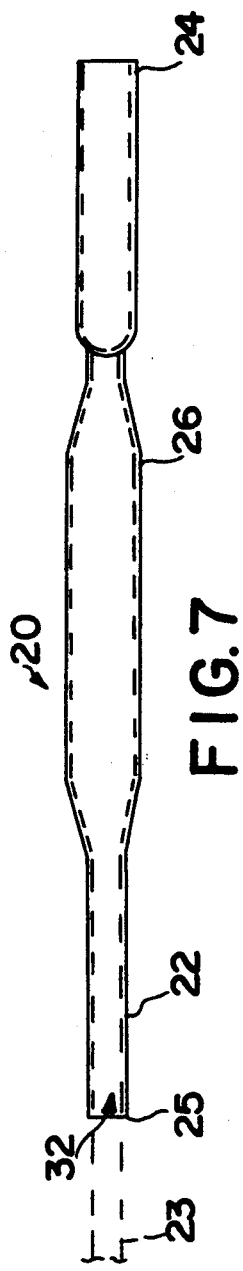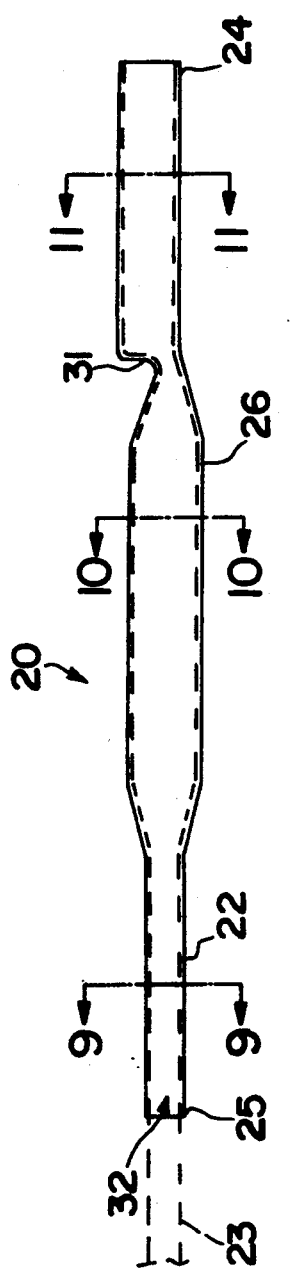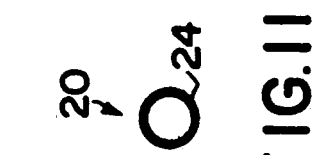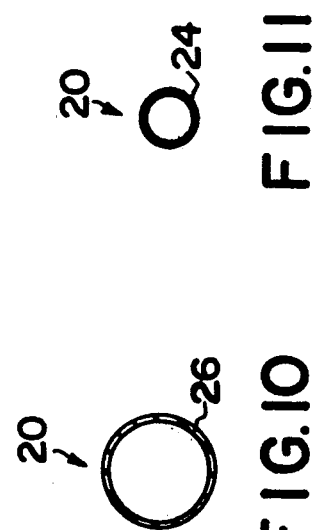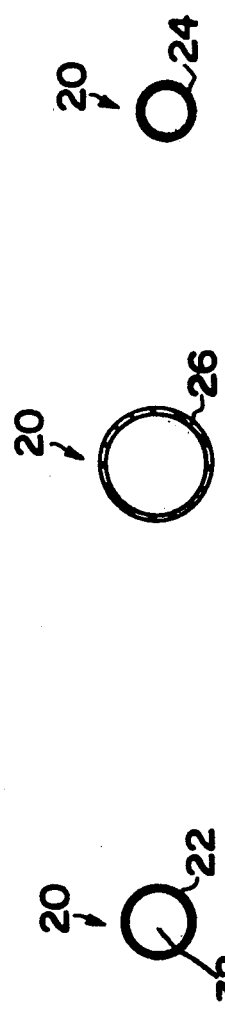

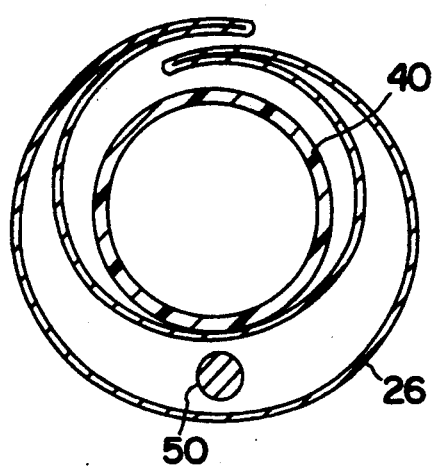
FIG. 17
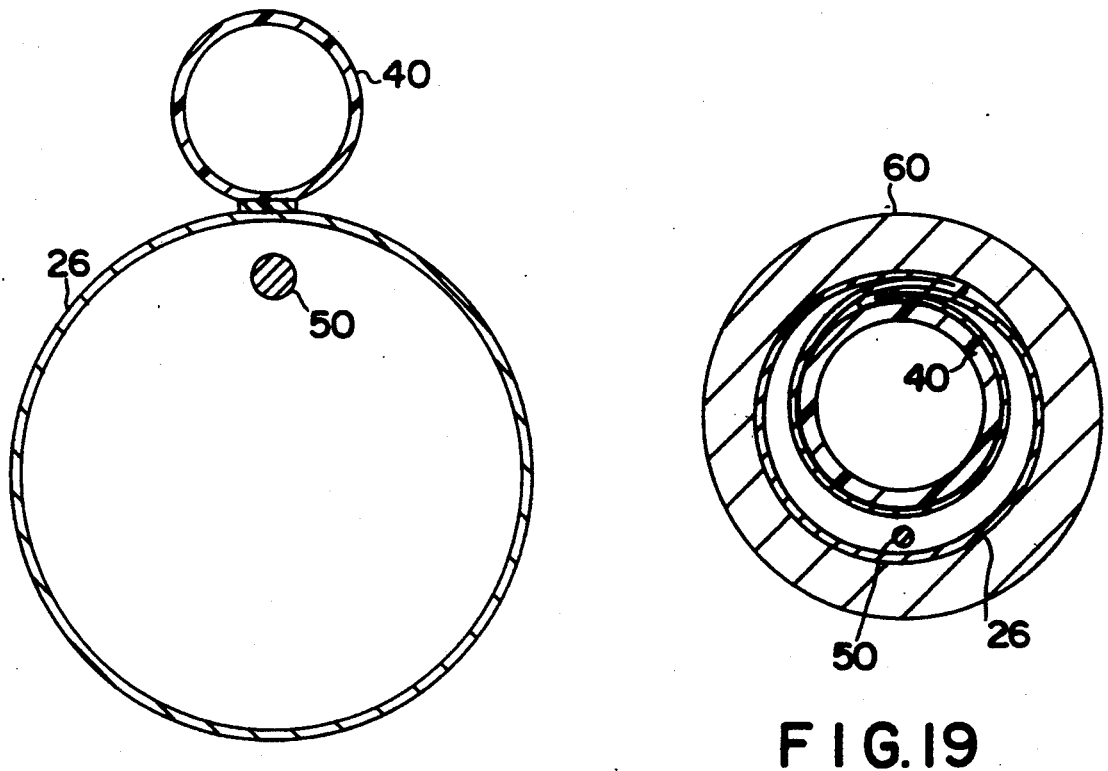
FIG. 18
FIG. 19

GROOVED BALLOON FOR DILATATION CATHETER

FIELD OF THE INVENTION

The present invention relates to the field of angioplasty, and more particularly relates to a balloon for a dilatation catheter.

BACKGROUND OF THE INVENTION

Percutaneous transluminal coronary angioplasty (PTCA) is widely accepted as an effective treatment of blockages in the coronary arteries. Blockages (stenoses) may occur from cholesterol precipitation on the coronary wall which may be in any stage from initial deposit through aged lesions. Coronary arteries can also become blocked due to formation of thrombus.

The most widely used percutaneous coronary angioplasty makes use of a dilatation balloon catheter. Typically, a guide catheter is employed to facilitate the introduction of the balloon catheter into the patient's vascular system. That is, the guide catheter is first introduced, and then the dilatation balloon catheter, with the balloon at its distal end in a deflated condition, is pushed through the lumen of the guide catheter until the balloon exits the distal end of the guide catheter. A guide wire coupled to the balloon catheter may be used to assist in pushing the balloon catheter through the guide catheter and in steering the distal end of the balloon catheter to the region of the stenosis or lesion. A radiographic contrast fluid is then fed under pressure through an inflation lumen of the dilatation catheter to the balloon, which causes the balloon to expand outward, thereby opening the stenosis.

In some angioplasty procedures, it is necessary to exchange one dilatation catheter for another. For this reason, dilatation balloon catheters are typically designed so that they are capable of being advanced and retracted along the guide wire.

One important characteristic of dilatation balloon catheters used for angioplasty is profile, i.e., the outer shape and diameter of a catheter's distal end portion when in a deflated condition. Considerable effort has been spent in developing low-profile dilatation balloon catheters by minimizing the dimensions of the core or inner tube which extends through the balloon to its distal end, and by reducing wall thickness, to the extent possible, of the balloon itself.

The outer diameter of the deflated distal end portion of a dilatation balloon catheter affects the ease and ability of the dilatation catheter to pass through the lumen of the guide catheter, through the coronary arteries, and across tight lesions.

A complicating factor in minimizing the deflated profile of a dilatation catheter balloon is that the balloon membrane is typically not distensible, i.e., it does not stretch or contract in response to changes in internal pressure. Thus, the balloon membrane has a constant surface area regardless of whether the balloon is inflated or deflated. Therefore, in order to reduce the outer diameter of the balloon in its deflated condition, it is common to fold the balloon flat, so that two wings or flaps are formed. These two wings are then brought together in some fashion, as by folding or wrapping, so as to reduce the overall diameter of the deflated balloon. Often, some sort of protective sleeve or sheath is disposed around the folded or wrapped balloon to protect the balloon from contamination or damage prior to its use.

In actual use, when inflation fluid is applied to the folded balloon, it causes the flaps to unwrap so that the balloon can inflate to its full inflated state.

Thus, it is desirable to minimize profile of any angioplasty balloon, or, in other words, to provide any inflated balloon diameter with the smallest possible profile. One practical effect is that the two flaps formed when the balloon is deflated and prepared for wrapping (during balloon protector installation) become very large relative to the core or inner tube of the catheter. The result is that it is difficult to get these two large flaps to fold together and squeeze out all of the space between them when folded, without damaging the catheter during balloon protector installation.

Various methods and balloon configurations have been proposed in the prior art for providing a dilatation balloon catheter having the lowest profile as possible when deflated and the largest possible diameter when inflated. One approach, which is suggested, for example, in U.S. Pat. No. 5,087,246 to Smith and in U.S. Pat. No. 5,147,302 to Euteneuer et al., is to provide a dilatation balloon which in deflated condition has more than two flaps or wings (for example, three wings) such that when the flaps or wings are wrapped circumferentially, the distance that each flap extends around the catheter is reduced compared with the conventional balloon configuration having only two flaps. The ease with which such flaps fold is also enhanced when their number is increased, such that when the balloon is deflated and withdrawn through the guide catheter following a procedure, the balloon more readily returns to its wrapped condition. The result is a reduced deflated profile given the same inflated diameter.

Another important characteristic of dilatation balloon catheters is the ease with which they can be advanced and retracted along a guide wire for the purposes of exchanging one catheter for another during an angioplasty procedure. In early dilatation balloon catheters, sometimes called "over-the-wire" catheters, the guide wire passed through the catheter along the catheter's entire length. U.S. Pat. Nos. 5,040,548 and 5,061,273 to Paul G. Yock, on the other hand, propose so-called "rapid-exchange" catheters having a guide wire lumen along a distal section of the catheter only. In the event that the dilatation catheter must be removed for the purposes of exchange, it is withdrawn along the guide wire, the guide wire being left in place in the vascular system. The distal end of a different dilatation catheter is then threaded onto the proximal end of the guide wire and advanced forward along the guide wire. When the guide wire is threaded only through a distal section of the dilatation catheter, there may be some reduction in friction between the catheter and the guide wire, and the length of the guide wire may also be reduced.

A similar approach is proposed in U.S. Pat. No. 4,762,129 to Bonzel (see also Reexamination Certificate B1 4,762,129). In the Bonzel patent, a "rapid-exchange" catheter is described in which a guide wire runs parallel with the inflation lumen of the catheter, and is threaded only through the distal end of the catheter, in the region of the balloon itself.

Catheters in accordance with the designs proposed in the above-referenced Yock '548 and '273 and Bonzel '129 patents have been commercially-available, and the construction of such catheters is well-known in the art.

While the above-described references may represent some improvement in field of balloon dilatation catheters, the inventor believes that there is an ongoing need for improvements in catheter design and preparation techniques, such that low (deflated) profile and large inflated balloon diameters may be achieved without sacrificing other characteristics. Additionally, it is believed that there is also an ongoing need for improvements which facilitate the rapid and efficient exchange of dilatation catheters during a procedure.

SUMMARY OF THE INVENTION

The present invention, therefore, is directed to a method and apparatus for providing a dilatation balloon catheter having a configuration which provides a low profile in an uninflated condition and which may be readily exchanged during an angioplasty procedure.

In accordance with one feature of the present invention, a dilatation catheter is provided with a balloon of a novel shape and configuration which enhances the qualities of low profile and ease of exchange. In particular, in one embodiment of the invention at least a central section of the balloon has a substantially semi-circular cross-section when in a deflated, unwrapped condition, such that the upper side of the balloon has a flattened configuration. Additionally, a groove is provided in this upper surface to accommodate an elongate cylindrical guide wire lumen as well as to improve wrap memory. When the balloon is inflated, it has a substantially round cross-section throughout.

In accordance with another feature of the present invention, a guide wire lumen can be provided which extends along only a distal section of the dilatation catheter, so as to facilitate rapid and easy exchange of the catheter during a procedure.

In accordance with still another feature of the present invention, the guide wire lumen is bonded into the groove in the upper surface of the balloon in such a way that the guide wire lumen is not required to bend or curve at that area. This too enhances the rapidity and ease of exchange.

In accordance with yet another feature of the present invention, the guide wire lumen extends through and into the balloon at a point substantially near the distal end of the groove provided in the balloon. A stepped shape or configuration of the balloon at the point of entry of the guide wire lumen eliminates the need for a curve to be imparted to the guide wire lumen as it enters the balloon.

Outside the balloon, the guide wire lumen extends toward the extreme distal end of the balloon and catheter. The distal end of the guide wire lumen and the distal end of the balloon is attached in a fluid-tight seal to the outside of the guide wire lumen at the distal end thereof. In this way, injection of fluid into the inflation lumen at the proximal end of the catheter generates an inflation pressure which inflates the balloon.

BRIEF DESCRIPTION OF THE DRAWINGS

The foregoing and other features of the present invention will perhaps be best understood with reference to the following detailed description of a specific embodiment of the invention, when read in conjunction with the accompanying drawings, wherein:

FIG. 2 is a top view of the balloon of FIG. 1 in an uninflated condition;

FIG. 3 is a side view of the balloon of FIG. 1 in an uninflated condition;

FIGS. 4, 5, and 6 are sectional views of the balloon from FIG. 3;

FIG. 7 is a top view of the balloon of FIG. 1 in an inflated condition;

FIG. 8 is a side view of the balloon of FIG. 1 in an inflated condition;

FIGS. 9, 10, and 11 are sectional views of the balloon from FIG. 8;

FIG. 17 is an end view of the balloon of FIG. 12 in an uninflated, wrapped condition;

FIG. 18 is an end view of the balloon of FIG. 12 in an inflated condition; and

FIG. 19 is an end view of the balloon of FIG. 17 within a balloon protector.

DETAILED DESCRIPTION OF A SPECIFIC EMBODIMENT OF THE INVENTION

Figure 1:
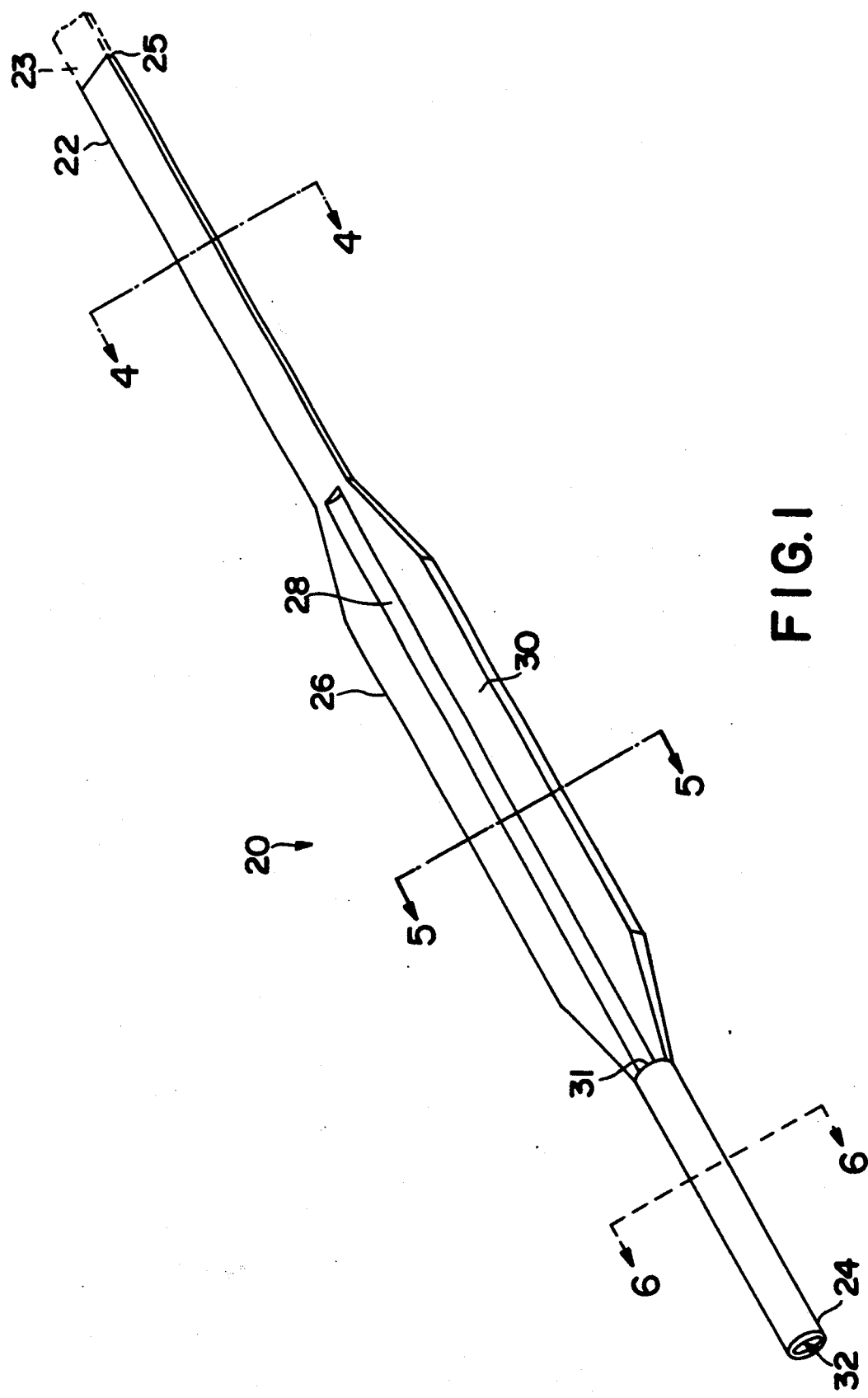
FIG. 1 is a perspective view of the balloon end of a dilatation balloon catheter in accordance with one embodiment of the present invention.

In the following description, an embodiment of the invention will be described in the context of a particular type of balloon dilatation catheter having a guide wire lumen extending along a distal section of the catheter. Those of ordinary skill in the art however, will appreciate that the invention may be advantageously practiced in the contexts of various types of catheters, whether of the "over-the-wire" type, the "rapid-exchange" type, or perfusion catheters as well as others. Furthermore, those of ordinary skill in the art will recognize that they can make adaptations to the embodiment discussed herein for other kinds of catheters used in a variety of applications including, but not limited to, those of veinous coronary, veinous non-coronary, or fallopian tube applications.

The Figures show the distal end of a balloon dilatation catheter, and in particular show a balloon portion 20. It is to be understood for the purposes of the following description that in the practice of the present invention, balloon 20 is coupled at its proximal end 22 to the distal end of a flexible elongate catheter 23 (a portion of which being shown in phantom in FIGS. 1–11) such that an internal lumen 32 extending throughout balloon 20 is contiguous with the lumen of catheter 23. The interface between the distal end of catheter 23 and the proximal section 22 of balloon 20 is designated with reference numeral 25 in the Figures. In this way, balloon 20 may be inflated with fluid injected into the proximal end (not shown) of catheter 23.

In the presently disclosed embodiment of the invention, catheter 23 is of the coiled wire type but those of ordinary skill in the art will recognize that other catheter bodies can be used such as polymer shafts. Balloon 20, to be hereinafter described in detail, is made of an elastic, biocompatible material such as PE, LLDPE, PET, POC, or the like.

Balloon 20 essentially has three sections: proximal section 22, a distal section 24, and a central section designated as 26 in the Figures. Those of ordinary skill in the art will appreciate that it is central section 26 of balloon 20 whose profile expands upon inflation and contracts upon deflation. The profiles of proximal section 22 and distal section 24 remain substantially uniform whether balloon 20 is inflated or deflated.

In the presently preferred embodiment of the invention, balloon 20 is made of polyethylene, although it is contemplated that other resilient materials may be suitable for the purposes of the invention.

FIGS. 1, 2, 3, 4, 5 and 6 show balloon 20 in an uninflated, unwrapped condition. In this condition, and in accordance with one aspect of the present invention, central section 26 of balloon 20 has a substantially semi-circular cross-section, as can be best appreciated with reference to FIG. 5, which is a sectional view of central section 26 of balloon 20. In addition, central section 26 is provided with an elongated groove 28 in a flat upper surface 30 extending between proximal section 22 and distal section 24 of balloon 20. As shown in FIG. 4, which is a sectional view of proximal end 22 of balloon 20, proximal end 22 also has a substantially semi-circular cross-section. It is to be understood, however, that the semi-circular cross-section of proximal section 22 arises as a fabrication expedient and is not believed to be an essential aspect of the present invention. As previously noted, the lumen designated as 32 in proximal section 22 is affixed to the distal end of flexible elongate catheter 23, so that fluid may be communicated along catheter 23 into lumen 32 in order to inflate central section 26 of balloon 20. Such attachment of proximal section 22 of balloon 20 to a catheter can be expected to impart a substantially circular cross-section to proximal end 22.

The distal end of groove 28 in central section 26 of balloon 20 lies substantially at the base of a stepped transition 31 between central section 26 and distal section 24 of balloon 20. Step 31 can be best observed in the side views of FIGS. 3 and 8.

FIGS. 7, 8, 9, 10, and 11 show balloon 20 in an inflated condition. As previously noted, such inflation is accomplished by injecting fluid into lumen 32 at proximal end 22. A comparison of FIGS. 6 and 11 reveals that the cross-section of distal section 24 of balloon 20 remains substantially unchanged when balloon 20 is inflated. As can be seen from FIGS. 4 and 9, the diameter of proximal end 22 also remains unchanged (although the incidentally semi-circular cross-section of proximal section 22 may be restored to more of a circular one, as shown). Central section 26, however, expands significantly, as can be appreciated through comparison of FIGS. 5 and 10.

Groove 28 in otherwise flat upper surface 30 of central section 26 of balloon 20 is provided in part to accommodate an elongate guide wire lumen 40 (not shown in FIGS. 1–11) which extends in parallel along the length of balloon 20 and along a distal portion of catheter 23, as will be hereinafter described in greater detail. As previously described, guide wires are typically used to facilitate insertion and steering of a dilatation balloon catheter assembly in a patient's vascular system. In the presently preferred embodiment of the invention, guide wire lumen 40 for receiving a guide wire designated with reference numeral 42 in the Figures) extends along a distal portion of the dilatation balloon catheter assembly comprising catheter 23 and balloon section 20. In particular, guide wire lumen 40 extends alongside catheter 23 and the proximal and central sections 22 and 26 of balloon 20, centrally through distal section 24 of balloon 20 to the extreme distal end of balloon 20, for an overall distance of approximately 30-centimeters.

It is contemplated that guide wire lumen 40 can be glued in place within groove 28. In accordance with one aspect of the present invention, the configuration of guide wire lumen 40 with respect to balloon 20 is such that lumen 40 is not subjected to curvature as it passes along the transition from proximal section 22 to central section 26 and into distal section 24, as will be hereinafter described.

Referring to FIGS. 12, 13, 14, 15, and 16, balloon 20, the distal end of catheter 23, and the distal ends of guide wire lumen 40 and guide wire 42 are shown in a cross-sectional side view (FIG. 12), and various sectional views (FIGS. 13–16). It is to be understood that views of FIGS. 12–16 are greatly enlarged, for the purpose of more clearly illustrating the presently disclosed embodiment of the invention, and are not drawn to scale. Those of ordinary skill in the art will appreciate that typical balloons have dimensions on the order of 20-mm or longer in length and 1.5- to 6.0-mm inflated diameter.

Figure 12:
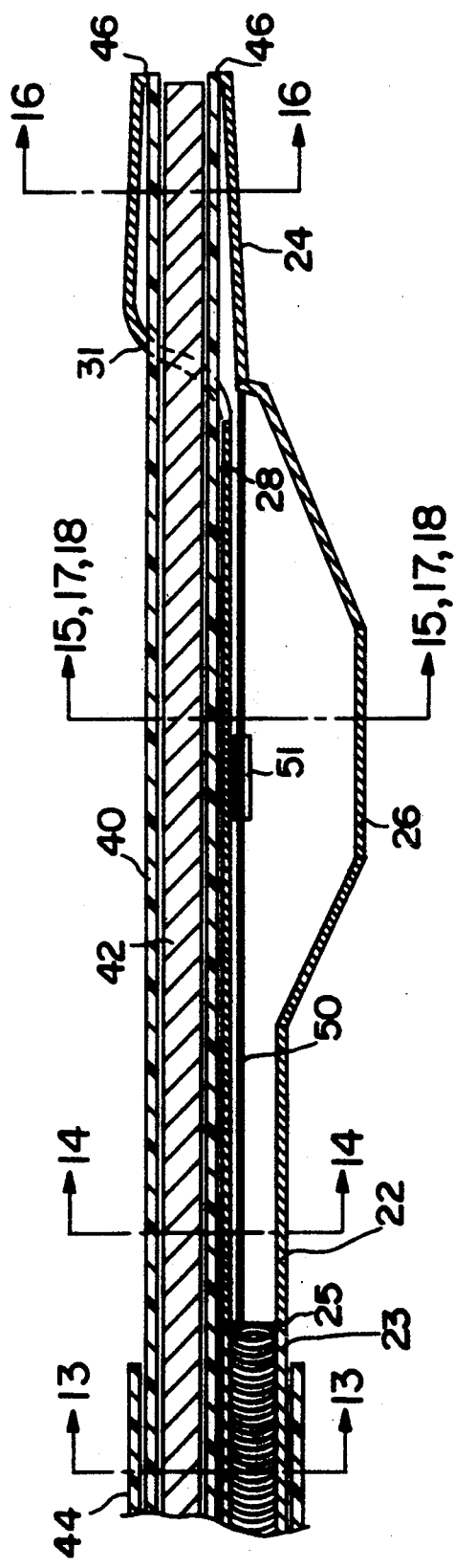
FIG. 12 is a sectional side view of the distal end of a catheter attached to the balloon of FIG. 1, with a guide wire lumen disposed on the catheter/balloon combination.
Figure 13:
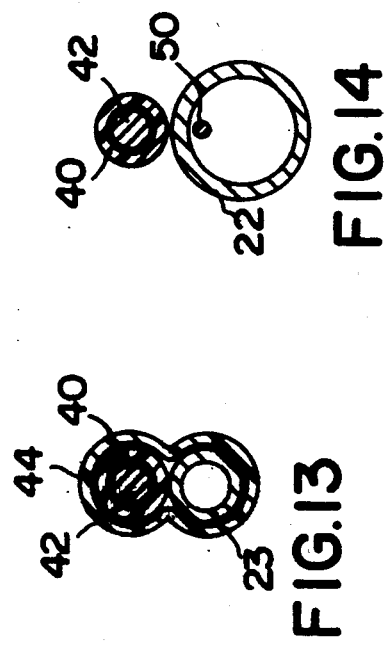
FIG. 13, 14, 15 and 16 are sectional views of the balloon and guide wire lumen combination from FIG. 12.

Referring to FIG. 12, beginning about 30-centimeters back from the distal end of catheter 23, guide wire lumen 40 is disposed on top of catheter 23. The guide-wire lumen extends proximally from the distal end of catheter 23 and should be at least 10 cm long. In one embodiment of the invention, guide wire lumen 40 and catheter 23 are laminated together with a polyethylene sheath 44, resulting in a substantially figure-eight cross section as shown in FIG. 13. The proximal end of guide wire lumen 40 (not shown) is left open. Sheath 44 extends from the proximal end of guide wire lumen 40 to a point near interface 25 between catheter body 23 and balloon 20, as shown in FIG. 12.

Figure 14:
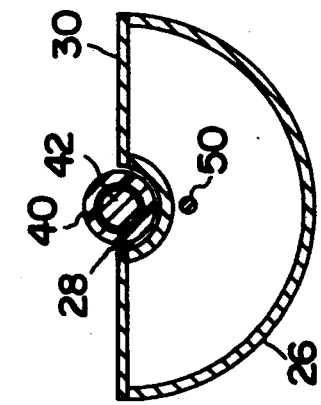
Figure 15:
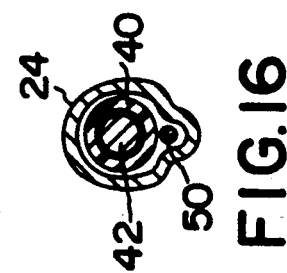

As previously described, and with continued reference to FIG. 12, an interface 25 is established between the distal end of catheter 23 and the proximal end 22 of balloon 20. Guide wire lumen 40 extends beyond the end of catheter 23 and thus is disposed on top of the distal section 22 of balloon 20. A sectional view of guide wire lumen 40, guide wire 42, and distal section 22 of balloon 20 is shown in FIG. 14.

Figure 16:
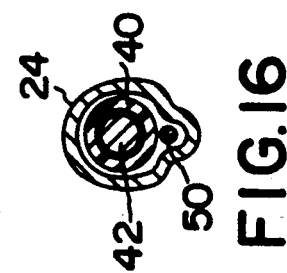

Guide wire lumen 40 further extends across central section 26 of balloon 20, and is attached with adhesive to groove 28. This may be best appreciated with reference to the sectional view of FIG. 15. In accordance with one aspect of the invention, an incision or skive is made in stepped transition 31 between central section 26 and distal section 24 of balloon 20. With reference again to FIG. 12, the skive in step 31 is made to enable guide wire lumen 40 to pass into the interior lumen defined by distal section 24 of balloon 20. Thus, the cross-section of the balloon/guide wire lumen combination in distal section 24 is as shown in FIG. 16. Guide wire lumen extends the length of distal section 24, and at the extreme distal end of distal section 24, a fluid-tight seal is established between balloon 20 and the outer circumference of guide wire tureen 40, at points designated as 46 in FIG. 12. A fluid-tight seal is also established at the skive in step 31 where guide wire lumen 40 enters distal section 24 of balloon 20.

FIG. 12 also shows a core wire 50, extending within balloon 20 from interface 25 between balloon 20 and catheter body 23 to distal section 24 of balloon 20. Core wire 50 may be coupled at its proximal end to the distal end of coiled-wire catheter body 23, and is bonded at section 24 of balloon 20. Core wire 50 adds some degree of support and rigidity to balloon 20 to facilitate manipulation thereof during use of the present invention. In the presently preferred embodiment of the invention, core wire 50 is made of stainless steel or the like and may be tapered from a larger diameter at interface 25 to a smaller diameter in distal section 24 of balloon 20.

In addition, FIG. 12 shows a marker band 51 made of tubular radiopaque material. As would be apparent to those of ordinary skill in the art, marker band 51 assists a clinician performing a procedure using balloon 20 to observe and properly position balloon 20 using radiographic techniques.

In accordance with one aspect of the present invention, the configuration of guide wire lumen 40 and balloon 20 described above with reference to FIGS. 1–16 allows balloon 20, particularly central section 26 thereof, to be wrapped into a very low profile around guide wire lumen 40. FIG. 17 is a sectional view of central section 26 of balloon 20 being wrapped around guide wire lumen 40. FIG. 18 shows central section 26 of balloon 20 in an inflated state, with guide wire lumen 40 bonded thereto.

FIG. 19 is a sectional view of the central section 26 of balloon 20 having been wrapped around guidewire lumen 40 with a balloon protector 60 inserted thereon. Heat sterilization of balloon 20 with protector 60 installed causes protector 60 to shrink in diameter, further compressing balloon 20 into its wrapped configuration.

Those of ordinary skill in the art will appreciate that different diameters of silicone tubing will be needed for different balloon types and sizes.;..." It has been the inventors' experimental experience that 0.0940 cm×0.216 cm (0.037-×0.085-inch) parylene-coated silicone tubing is effective to wrap and heat-set 2.5 mm size balloons. Heat-setting has been performed at 37° C. for 10 minutes in a dry heat station.

From the foregoing detailed description of a specific embodiment of the invention, it should be apparent that a balloon for a dilatation balloon catheter and a novel configuration of a balloon and guide wire lumen has been disclosed. Although a specific embodiment of the invention has been described herein in some detail, this has been done for the purposes of illustration only, and is not intended to be limiting with respect to the scope of the invention. It is contemplated that various substitutions, alterations, and/or modifications, including but not limited to those specifically noted hereinabove, may be made to the disclosed embodiment of the invention without departing from the spirit and scope of the invention as defined in the appended claims, which follow.

What is claimed is:

1. A dilatation catheter, comprising:
   an elongate catheter body;
   a balloon having a proximal section with a proximal end and a distal end, a central inflatable section with a proximal end and a distal end, and a distal section with a proximal end and a distal end, the distal end of the proximal section being affixed to the proximal end of the central inflatable section and the proximal end of the distal section being affixed to the distal end of the central inflatable section,
   the balloon being disposed on the distal portion of said catheter body and inflatable through a lumen in said catheter body, said balloon having an outer surface and an elongate groove formed on one side, of said outer surface the groove having a proximal end and a distal end; and
   a tube defining a guidewire lumen, coupled to and coextensive with at least a distal section of said elongate catheter body said tube defining said guide wire lumen being received in said groove so that when said balloon is uninflated, said guide wire lumen can adopt an essentially straight configuration in the region of the balloon and wherein said tube defining said guide wire lumen passes through a surface of said balloon and extends within the distal section of said balloon.

2. A dilatation catheter, comprising:
   an elongate catheter body;
   a balloon having a proximal section with a proximal end and a distal end, a central inflatable section with a proximal end and a distal end, and a distal section with a proximal end and a distal end, the distal end of the proximal section being affixed to the proximal end of the central inflatable section and the proximal end of the distal section being affixed to the distal end of the central inflatable section,
   the balloon being disposed on the distal portion of said catheter body and inflatable through a lumen in said catheter body, said balloon having an outer surface and an elongate groove formed on one side, of said outer surface the groove having a proximal end and a distal end; and
   a tube defining a guidewire lumen, coupled to and coextensive with at least a distal section of said elongate catheter body said tube defining said guide wire lumen being received in said groove so that when said balloon is uninflated, said guide wire lumen can adopt an essentially straight configuration in the region of the balloon and wherein said tube defining said guide wire lumen passes through a surface of said balloon in the region of the distal end of said groove into said distal section of said balloon.

3. A dilatation catheter, in accordance with claim 2 wherein said distal section of said balloon is offset with respect to said inflatable section, such that said guide wire lumen adopts a substantially straight configuration as it passes into a surface of said balloon.

* * * * *